(12) United States Patent
Miller et al.

(10) Patent No.: US 6,945,961 B2
(45) Date of Patent: Sep. 20, 2005

(54) INJECTION DEVICE

(75) Inventors: Thomas Dedenroth Miller, Copenhagen (DK); Claus Schmidt Moller, Fredensborg (DK); Steffen Hansen, Hillerod (DK)

(73) Assignee: Novo Nordisk A/S, Bagsvaerd (DK)

( * ) Notice: Subject to any disclaimer, the term of this patent is extended or adjusted under 35 U.S.C. 154(b) by 126 days.

(21) Appl. No.: 10/611,389

(22) Filed: Jul. 1, 2003

(65) Prior Publication Data

US 2004/0064104 A1 Apr. 1, 2004

Related U.S. Application Data

(60) Provisional application No. 60/401,545, filed on Aug. 6, 2002.

(30) Foreign Application Priority Data

Jul. 10, 2002 (DK) ........................ 2002 01084

(51) Int. Cl.[7] ................................ A61M 5/00
(52) U.S. Cl. ................ 604/207; 604/208; 604/211; 604/218; 604/223; 604/224; 604/232
(58) Field of Search ................ 604/232, 220, 604/228, 229, 71, 246, 181, 186–187, 207–211, 218, 223–225; 222/309, 390, 391

(56) References Cited

U.S. PATENT DOCUMENTS

| 4,883,101 | A |   | 11/1989 | Strong ........................ 141/27 |
| 5,279,585 | A | * | 1/1994  | Balkwill ..................... 604/207 |
| 5,938,642 | A | * | 8/1999  | Burroughs et al. ......... 604/208 |
| 5,947,934 | A |   | 9/1999  | Hansen et al. .............. 604/207 |

FOREIGN PATENT DOCUMENTS

| EP | 554996       | 8/1993  |
| EP | 702970       | 3/1996  |
| WO | WO 01/54757  | 8/2001  |
| WO | WO 01/83008  | 11/2001 |

\* cited by examiner

*Primary Examiner*—Nicholas D. Lucchesi
*Assistant Examiner*—Catherine S. Williams
(74) *Attorney, Agent, or Firm*—Marc A. Began, Esq.; Reza Green, Esq.; Richard W. Bosk, Esq.

(57) ABSTRACT

An injection device having an incremental clicking mechanism providing the user with an indication of the number of doses being set. For handling different types of medicaments having different dose volumes in the same type of injection device it is beneficial to provide an additional clicking mechanism which is easy changeable. The clicking mechanism is preferably a curved track provided between the dose setting member and a non-rotatable clicker element.

2 Claims, 7 Drawing Sheets

INJECTION DEVICE

CROSS REFERENCE TO RELATED APPLICATIONS

This application claims priority under 35 U.S.C. 119 of Danish application no. PA 2002 01084 filed Jul. 10, 2002, and U.S. provisional application No. 60/401,545 filed Aug. 6, 2002; the contents of both are fully incorporated herein by reference.

THE TECHNICAL FIELD OF THE INVENTION

The invention relates to injection devices of the kind comprising a housing accommodating a cartridge, a dose setting and injection mechanism, a rotatable dose setting member coupled to the dose setting and injection mechanism, and an injection button coupled to the dose setting and injection mechanism and by which a piston rod drive can be activated for advancing the piston forward to press out a set dose through a conduit connected to the cartridge.

DESCRIPTION OF RELATED ART

A prior art injection device of this kind is disclosed in WO 01/83008. This injection device comprises of three basic parts; a dose setting and injection mechanism, a dose setting member and an injection button.

The dose setting and injection mechanism of this prior art injection device is best shown in FIG. 4 of WO 01/83008. When a dose is being set, the coupling ring (29) is rotated by the arm (32). During this rotation the barb (40) rides over the barbs (41) of the driver (27) which produces a clicking and audible sound. At the same time the bulging ends (43, 44) of the coupling ring (29) also makes an audible sound by riding over the barbs (45) on the inside surface of the rod guiding part (20). The driver (27) and the guiding part (20) are both provided with the same number of barbs, such that the produced audible sounds amplify each other. The barbs also work as incremental clicks indicating the number of set doses. The number of barbs or clicks are set to equal the dose scale of the injection device, such that one barb or click is dedicated each single dose setting. For the particular injection device shown in WO 01/83008 the number of barbs or clicks is 60 such that the scale, which scale indications correlate with the barbs or clicks, resembles the scale of an ordinary clock bearing 60 scale indications on one full circle. All though in same cases the full circle is not used and henceforth there are fewer scale indications.

This prior art injection device is to be used by diabetics needing regular injections of insulin. The distance between each barb is therefore set to correlate with one international unit of insulin (1 IU). In this way the user will feel and hear one incremental click for each international unit being set. Insulin is typically made with 100 international units (IU) pr. millilitre of insulin.

DESCRIPTION OF THE INVENTION

This prior art injection device has proven itself very attractive to people suffering from diabetes. Due to the number of barbs, the prior art injection device is only suitable for one particular type of fluid medicament, since the tactile guidance is incorporated in the distance between the barbs and in the number of barbs. The prior art injection device is particular suitable for a fluid medication which are injected in a dose regimen requiring fine adjustment of the dose setting.

If an injection device of the type described in WO 01/83008 is to be used for other types of medicaments which has to be injected in a different dose volume e.g. with larger increment dose volumes, it will be necessary to redesign at least the dose setting and injection mechanism, such that the number of barbs of the new dose setting and injection mechanism correlates with the size of these new dose volumes.

This is however rather cumbersome, since it requires a different injection device, or at least a different dose setting and injection mechanism for each type of medicament.

The present invention aims to solve the problem of handling different types of medicaments being injected in different dose volumes or in different concentrations by providing the injection device with additional clicking means provided between the rotatable dose setting member and a non-rotatable clicker element, which clicking mechanism provides clicks that corresponds to a new dose volume, as defined in claim 1.

The general concept of the present invention is to provide an additional clicking mechanism which overrides the general clicking mechanism of the injection device. This has the advantages that the tactile and audible feedback of the injection device can be easily changed with out changing the underlying injection mechanism.

An injection device for insulin is usually provided with a tactile and audible feedback that correlates to international units of insulin, such that the user is provided with one click for each international unit being set.

According to claim 1, the injection device can now be utilized for a number of different fluid medicaments or concentrations of medicaments only by changing the dose setting member as long as the additional dose setting clicks provided from the interaction between the dose setting member and the non-rotatable clicker element is a multiplication of the underlying clicks provided by the dose setting and injection mechanism.

In this way the same injection device with the same dose setting and injection mechanism can be utilized for a number of different fluid medicaments or concentrations of medicaments only by changing the dose setting member.

When as disclosed in claim 2, the clicking means comprises a curved track provided as a part of the rotatable dose setting member, which curved track engages a non-rotatable clicker element provided on or as a part of the injection device, it is ensured that the distance between the indentations making up the curve can be designed quit freely.

When the curved track is provided on the periphery of the rotatable dose setting member as specified in claim 3 and the clicker element is a protrusion provided either on the housing as specified in claim 4 or on the dose setting and injection member as specified in claim 5, a very clear and distinct tactile guidance is obtained.

When as disclosed in claim 6, the protrusion is carried on a flexible arm, it is ensured that the rotatable dose setting member can be easy rotated.

The spaced indentations specified in claim 7 define the size of the dosage. These indentations should be a multiplication of the underlying smaller incremental clicks provided by the interaction between the barbs on the coupling ring and the outer toothing on the driver.

If the underlying incremental clicks represent international units of insulin it will be beneficial if a full circle represents 60 units. If the doses of medication to be injected by the new injection device is e.g. five time higher, the number of indentations then needs to be 12 indentations on a full circle.

It is however not necessary to provide the full number of indentations. With some medicaments there are a limit to the number of doses that can be injected at one time thus it is not necessary to provide more indentations than the maximum allowed number of doses.

As specified in claim 8, the preferred range of indentations is from 5 to 60. 60 indentations are preferred when the injection device is to be used for U 100 insulin. In this case the additional clicking will follow and amplify the underlying injection mechanism.

If one new dosage equals 10 international units of insulin a total of 6 indentations will be needed on a full circle. Prior to injecting the fluid medicament it is customary to make a so called air shot in order to empty the ampoule for air trapped inside the ampoule. An air shot is usually done by holding the device in a vertical upright position and deliver one unit. However, if one indentation representing one new dose of medicament contains 10 international units a large amount of medicament will be wasted. It is therefore preferred as specified in claim 9 to provide an air shot indentation located between the first and the second ordinary indentation. The size of the air shot defined by the location of the air shot indentation can be freely designed.

When as disclosed in claim 10, the rotatable dose setting member is provided with a scale where the indications correlate to the indentations, it is ensured that the user beside the tactile and the audible incremental feedback also is provided with a visual indication.

BRIEF DESCRIPTION OF THE DRAWINGS

The invention will be explained more fully below in connection with a preferred embodiment and with reference to the drawings in which.

DETAILED DESCRIPTION OF EMBODIMENT

FIGS. 1–4 shows the dose setting and injection mechanism 1 known from WO 01.83008.

Figure 1:
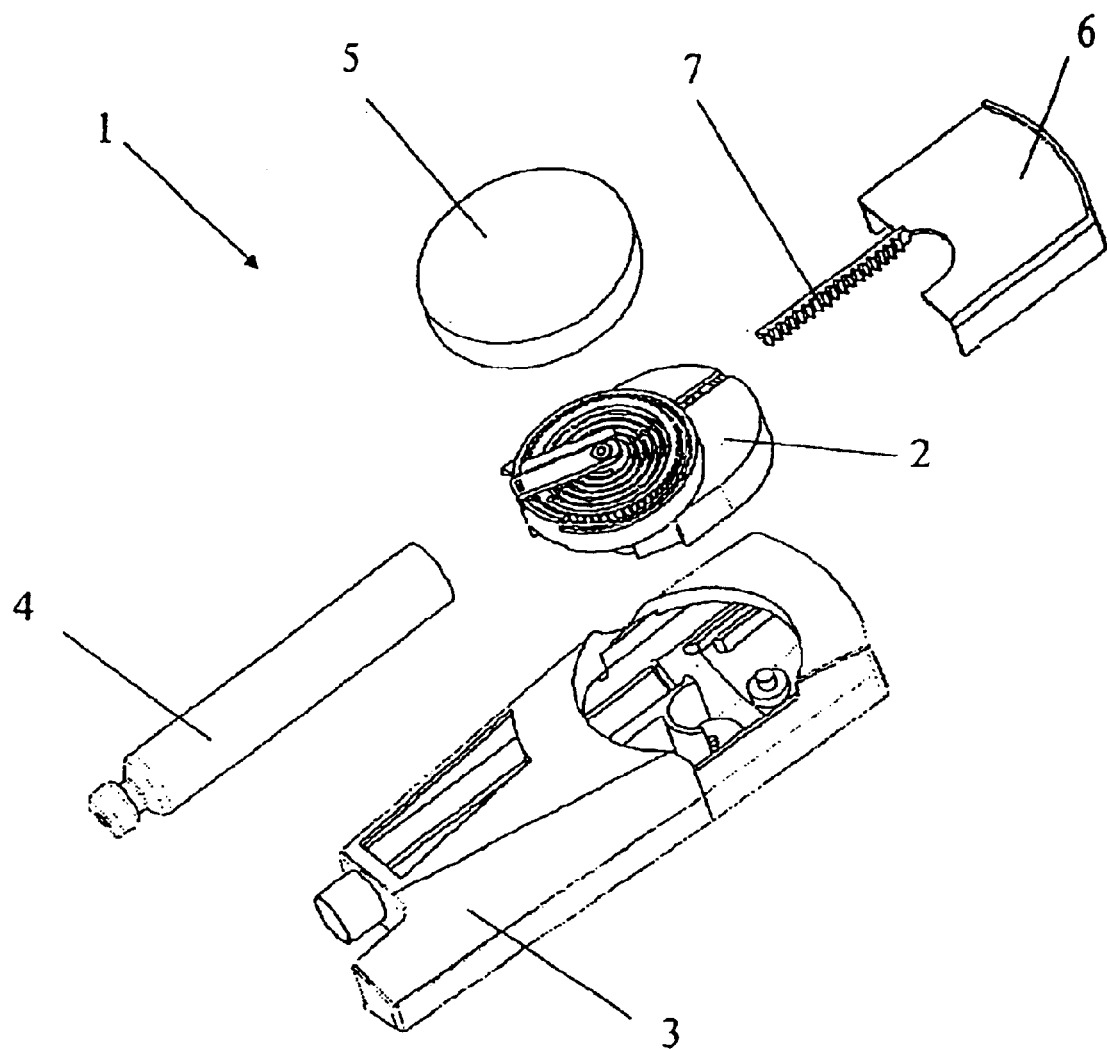
FIG. 1 Shows an exploded view of the prior art injection device
Figure 2:
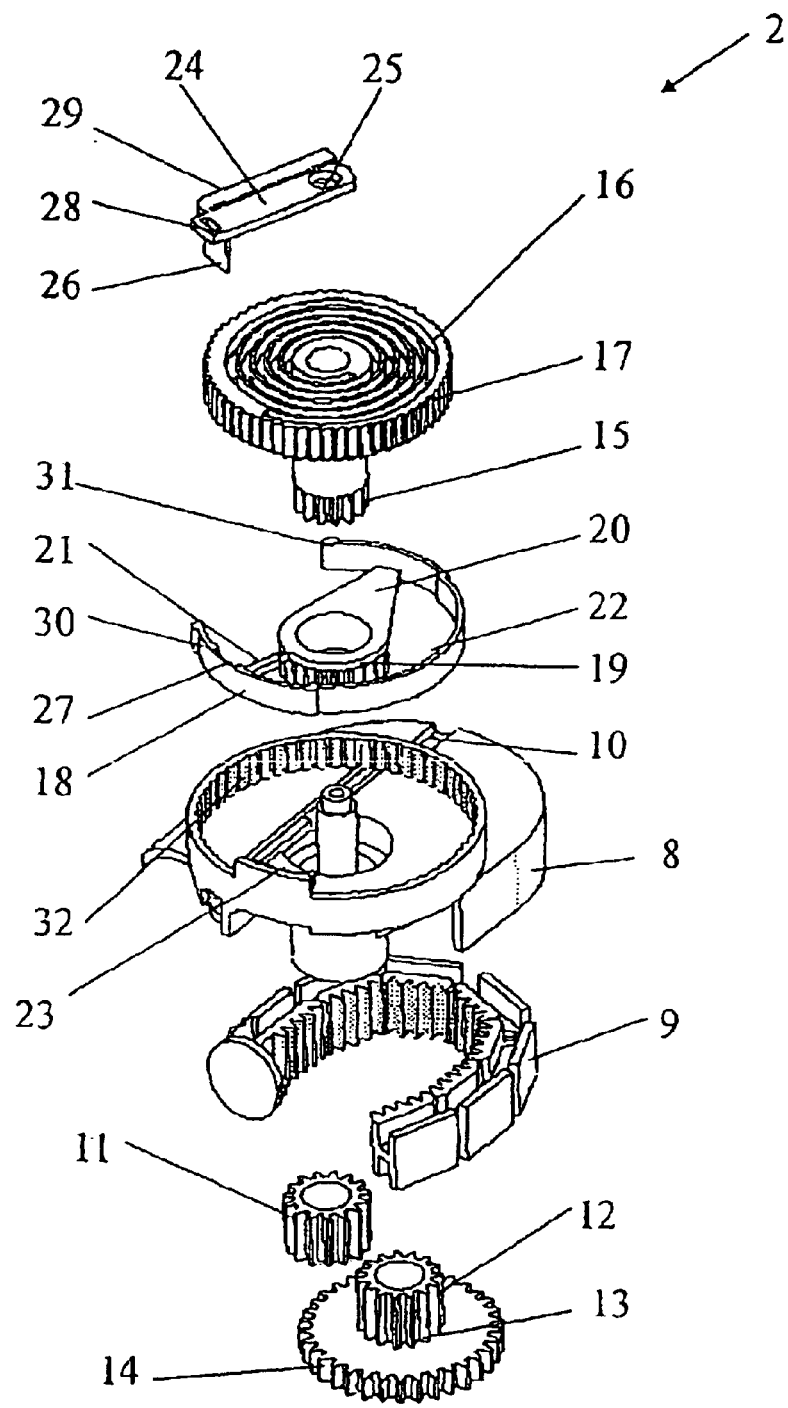
FIG. 2 Shows an exploded view of the dose setting and injection mechanism of the prior art injection device.
Figure 3:
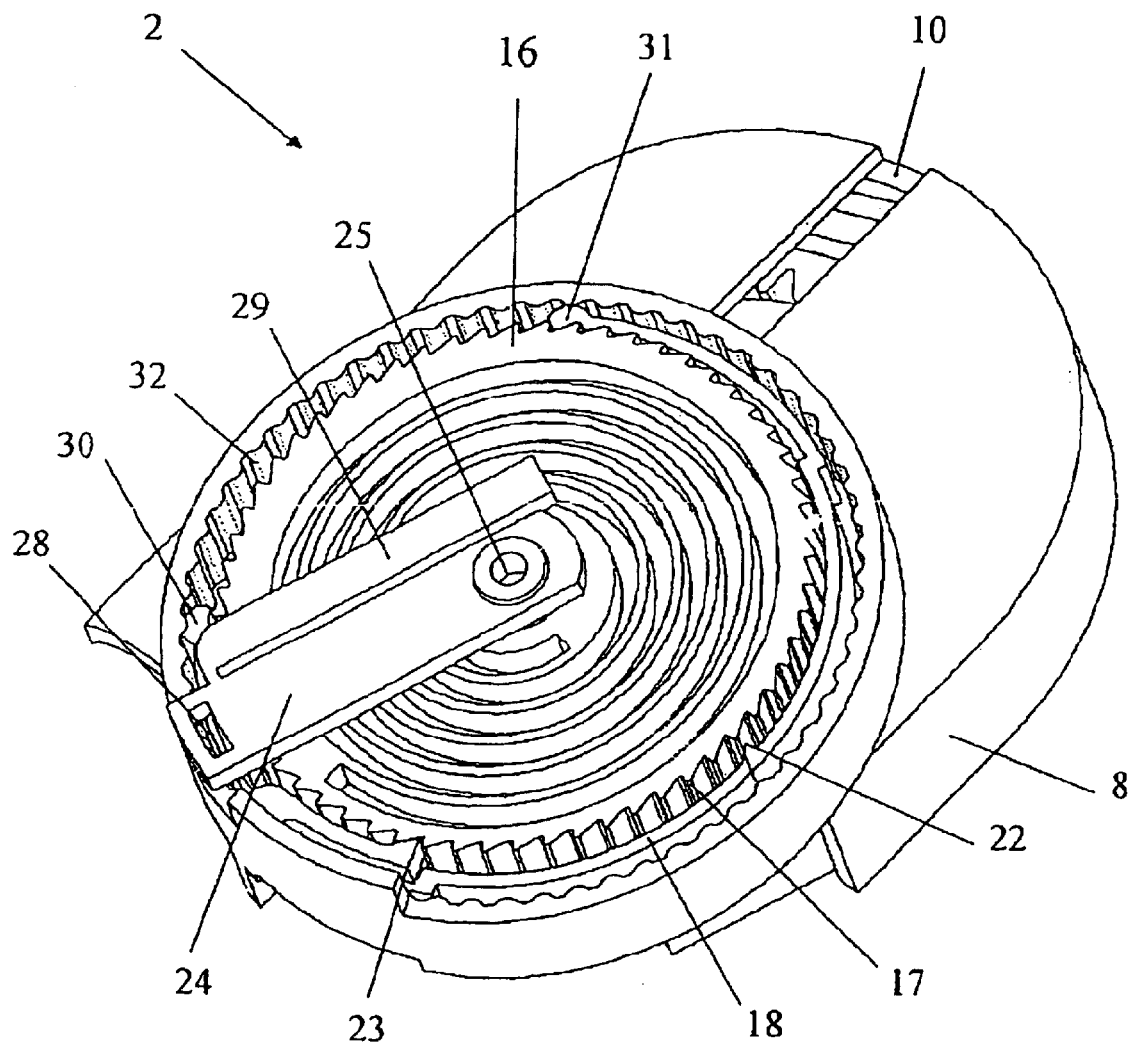
FIG. 3 Shows a schematically top view of the dose setting and injection mechanism of the prior art injection device.
Figure 4:
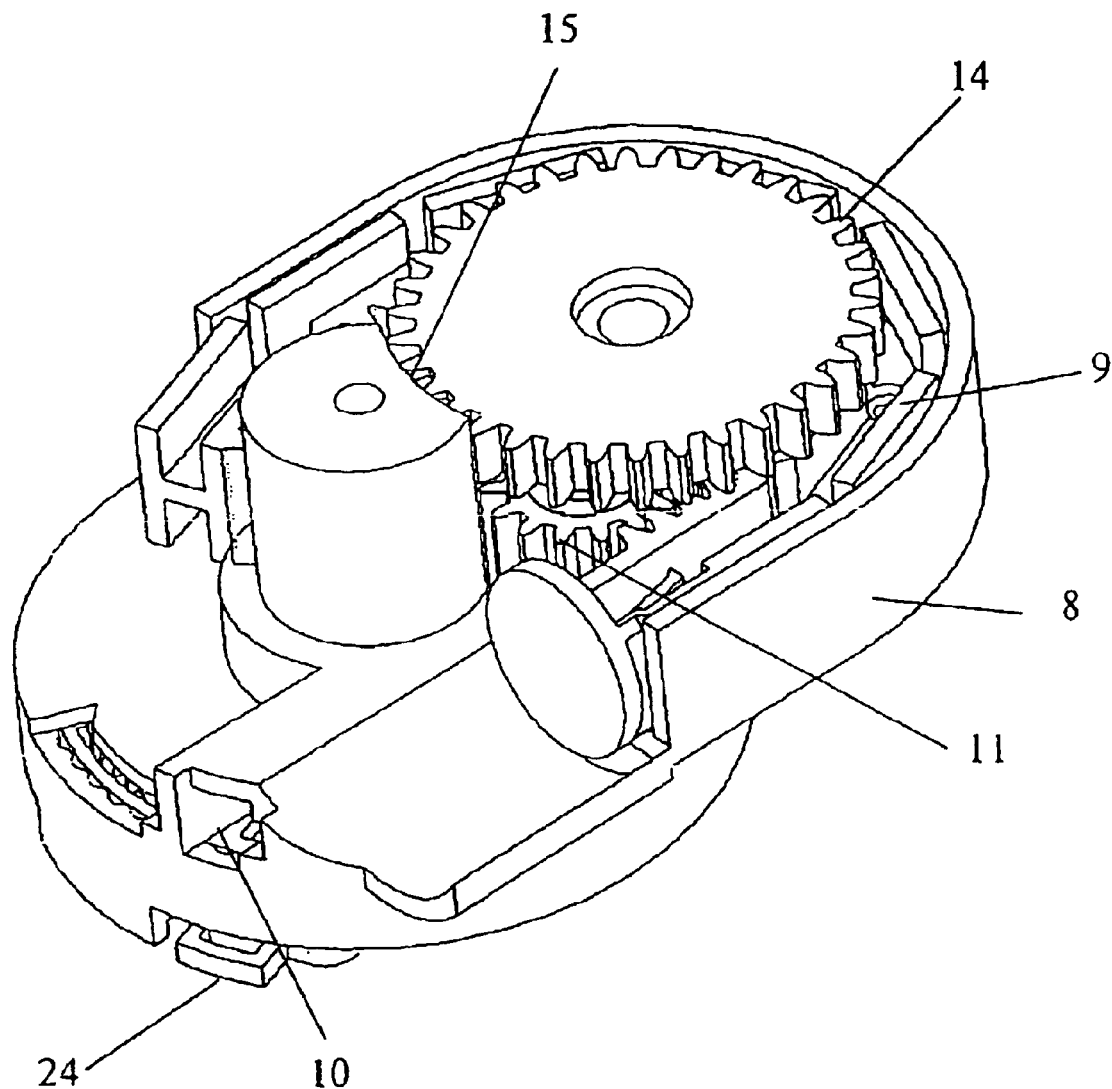
FIG. 4 Shows a schematically bottom view of the dose setting and injection mechanism of the prior art injection device.

The injection device 1 disclosed in FIG. 1 comprises a dose and injection mechanism 2 insertable into a housing 3. Also insertable into the housing 3 is the cartridge 4 containing the fluid medicament. A dose setting button 5 and an injection button 6 is connected to the dose and injection mechanism 2 inside the housing 3. The injection button 6 is provided with a toothed rack 7, which operates the dose and injection mechanism 2 to deliver a dose.

This prior art dose setting and injection mechanism 2 comprises a rod guiding part 8 in which a flexible piston rod 9 is guided. The rod guiding part 8 has a slot 10 into which the toothed rack 7 of the injection button 6 is guided. The flexible piston rod 9 is driven by a first gear wheel 11, which again is driven by the hub-wheel 12 of the second gear wheel 13. The second gear wheel 13 is made up from an outer toothed wheel 14 which is integral with the hub-wheel 12. The outer toothed wheel 14 is driven by the toothed axis 15 on the driver 16. This driver 16 has an outer tooting 17, which is located inside a coupling ring 18. The coupling ring 18 is provided with a coupling ring wheel 19, which is driven by the toothed rack 7 of the injection button 6 when a dose is being injected.

The coupling ring wheel 19 is connected to coupling ring 18 through a rigid part 20 and a more flexible part 21. The coupling ring 18 has on its inside surface one or more barbs 22, which interconnects with the outer tooting 17 of the driver 16, such that the driver 16 is driven by the coupling ring 18 in one direction, but not necessarily in the opposite direction.

A protrusion 23 provided on an inside surface of the rod guiding part 8 prevents the driver 16 from rotation in one direction. The direction in which the driver 16 can move freely is the direction in which the piston rod 9 is moved forward in the cartridge 4.

An arm 24 is at the centre 25 connected to the central portion of the rod guiding part 8. On the other end, the arm 24 is equipped with a cam 26 interacting with a notch 27 provided at the rim of the coupling ring 18. The arm 24 also has a depression 28, which is operational connected to the dose setting button 5, such that the arm 24 is rotated around the central portion of the rod guiding part 8 when the dose setting button 5 is rotated to set a dose.

A second arm 29 is situated parallel to the first arm 24 and is permanently connected thereto through a flexible beam. The second arm 29 bears on its backside a not shown cam, which cam is movable locked in the spiral shaped track of the driver 16. In this way, the number of rotations the driver 16 can perform relatively to the second arm 29 is limited to the length of the spiral shaped track. The total length of this track is adapted to the total amount of medicine in the cartridge 4 thereby ensuring that a dose larger than the amount of medicine remaining in the cartridge 4 can not be set.

When operating the injection device, the dose is set by turning the dose setting button 5 in the clockwise direction. The arm 24, which is operational connected to the dose setting button 5 rotates simultaneously. The notch 26 on the arm 24 rotates the coupling ring 18 too. Since the coupling ring wheel 19 interacts with the toothed rack 7 of the injection button 6, this injection button 6 is lifted away from the housing 3. Due to the protrusion 23, the driver 16 is prevented from rotating.

When the coupling ring 18 rotates, the bulging ends 30, 31 rides over the toothed surface 32 of the rod guiding part 8. The injection device shown in FIGS. 1–4 is to be used by diabetics needing regular injections of insulin. Therefore the distance between each of the indentations making up the toothed surface 32 corresponds to one international unit of insulin (1 IU). In this way the user can feel every increment being set when rotating the dose setting button 5. In addition an audible sound is produced when the bulging ends 30, 31 ride over the toothed surface 32. The incremental feeling and the incremental sound follows the number of indentations on the toothed surface 32.

The barb 22 on the coupling ring 18 rides over the outer toothing 17 of the driver 16 when a dose is set, which adds to the incremental feeling and to the incremental sound.

When delivering the set dose, the injection button 6 is pressed home. The toothed rack 7 of the injection button 6 then rotates the coupling ring wheel 19. The barb 22 interacts with the outer toothing 17 of the driver 16 hence rotating the driver 16 in the anti-clockwise direction. The rotation of the driver 16 is transmitted through the second gear wheel 13 to the first gear wheel 11, which first gear wheel 11 engages the piston rod 9. Rotation of the first gear wheel 11 causes the piston rod 9 to move forward inside the cartridge 4 thereby expelling the set dose of medicine through a not shown conduit connected to the distal end of the cartridge 4.

If a set dose is regretted, the dose setting member 5 is rotated in the anti clockwise direction. Due to the flexible part 21 of the coupling ring 18, the coupling ring 18 expands outwardly when rotated anti clockwise, allowing the barb 22 to slide over the outer toothing 17 of the driver 16. Hence the driver 16 is not affected by this backward rotation of the coupling ring 18.

Figure 5:
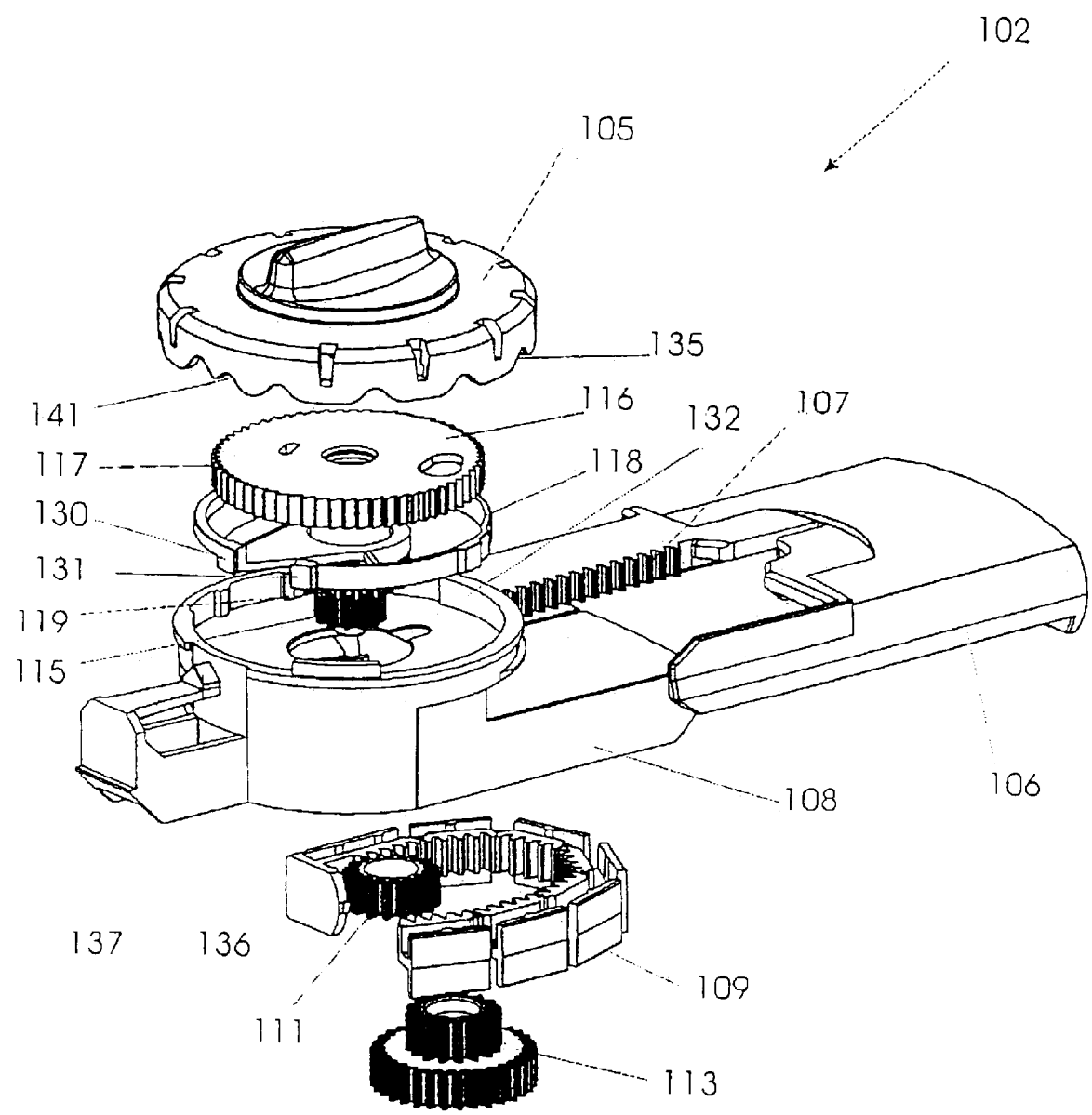
FIG. 5 Shows an exploded view of the dose setting and injection mechanism according to the invention.
Figure 6:
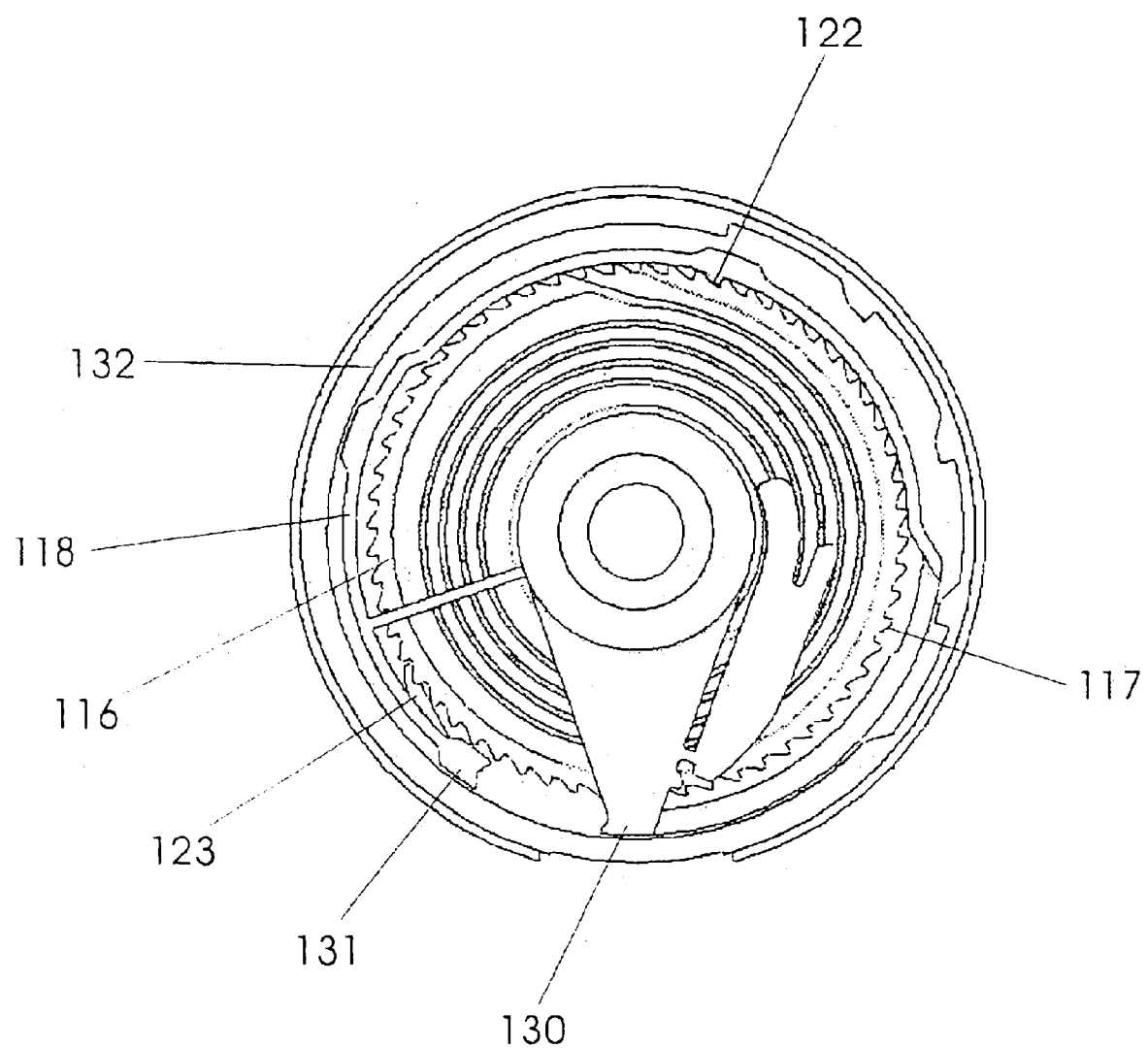
FIG. 6 Shows a cross sectional view through the dose setting and injection mechanism according to the invention.

FIGS. 5–6 discloses a dose setting and injecting mechanism 102 according to the invention. The toothed rack 107 of the injection button 106 engages the coupling ring wheel 119 through a slot in the rod guiding part 108. The coupling ring wheel 119 is integral with the coupling ring 118, which coupling ring 118 engages the driver 116. This engagement is made by one or more barb 122 located on the inside surface of the coupling ring 118 engaging the outer toothing 117 of the driver 116.

A protrusion 123 provided on an inside surface of the rod guiding part 108 prevents the driver 116 from rotation in one direction. The direction in which the driver 116 can move freely is the direction in which the piston rod 109 is moved forward inside the cartridge 104.

On the flipside of the rod guiding part 108, the toothed axis 115 of the driver 116 engages the second gear wheel 113. The second gear wheel 113 engages the first gear wheel 111 which transmits the rotational movement to the piston rod 109.

The inside surface 132 of the rod guiding part 108 is left as a smooth surface without any indentations. The bulging ends 131, 132 of the coupling ring 118 slides along this smooth inside surface 132 when a dose is set. As a result of this the incremental feedback delivered to the user from the dose setting and injection mechanism 102 of the injection device 1 is very gentle. Only a very silent clicking sound coming from the barbs 122 sliding over the outer toothing 117 of the driver 116 is heard when a dose is set.

Instead of the incremental guidance being a part of the dose setting and injecting mechanism 102 alone, this guidance is now overridden by the interaction between the dose setting button 105 and a non-rotatable clicker element 136, as will be explained in the following.

The dose setting button 105 is on the surface pointing towards the rod guiding part 108 provided with a number of indentations 135. The rod guiding part 108 is provided with a protrusion 136, which interacts with the dose setting button 105 when the injection device 1 is assembled. The protrusion 136 is located on a resilient arm 137 which is integral with the rod guiding part 108, but could as well be located on the housing.

When the dose setting button 105 is rotated the interaction between the indentations 135 of the dose setting button 105 and the protrusion 136 will provide the user with a tactile feedback containing both an incremental click feeling and an incremental click sound.

Even if the inside surface 132 of the rod guiding part 108 is toothed as known from the prior art, the interaction between the indentations 135 of the dose setting button 105 and the protrusion 136 will override the incremental clicks here provided, such that the user will feel the incremental clicks of the dose setting button 105 stronger than the incremental clicks provided by a toothing of the surface 132.

Figure 7:
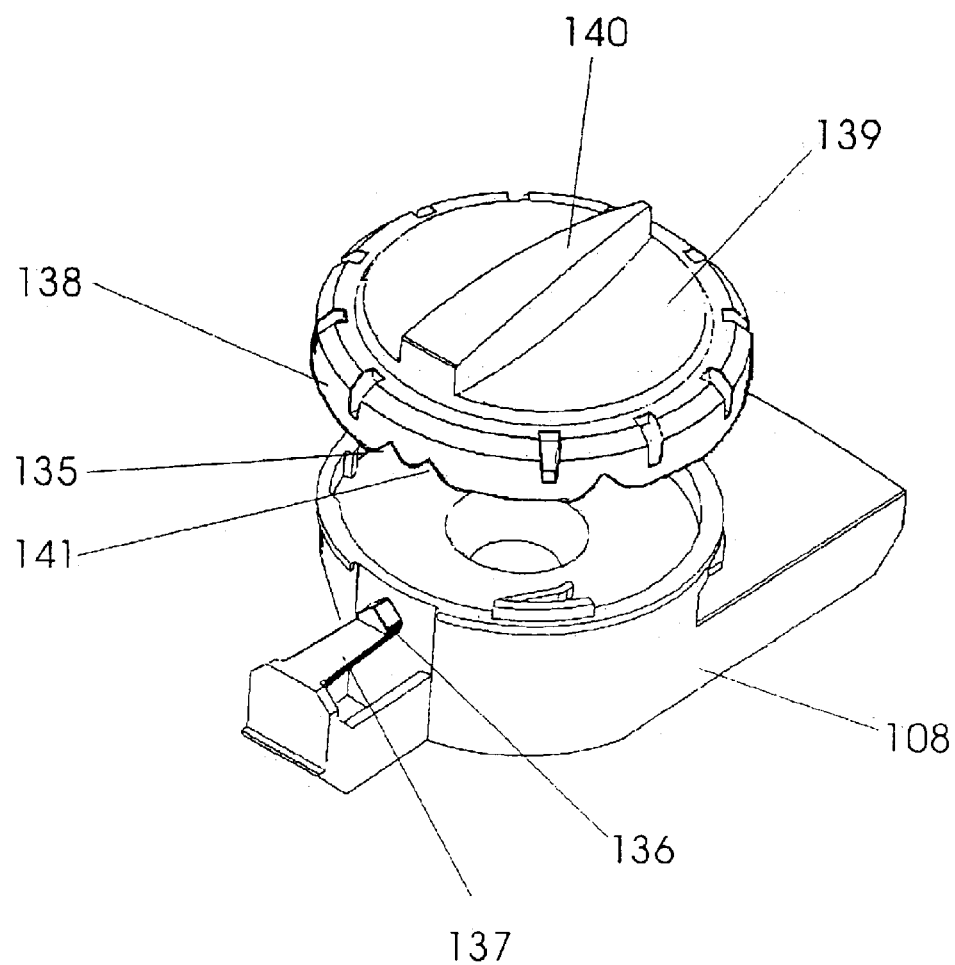
FIG. 7 Shows the dose setting and injecting mechanism according to the invention with the dose setting button.
Figure 8:
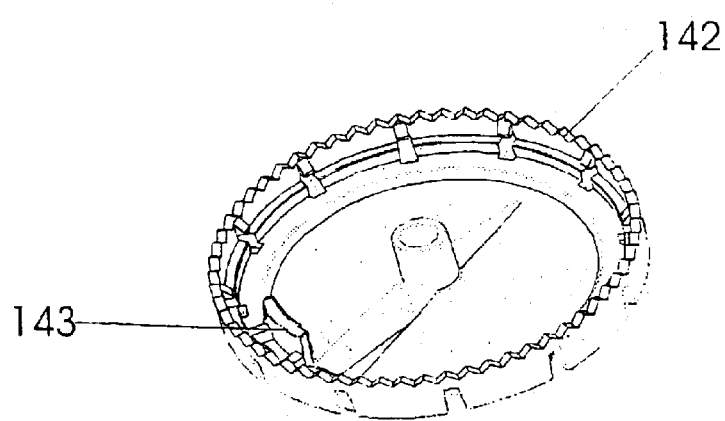
FIG. 8 Shows the dose setting button according to an embodiment of the invention The figures are schematic and simplified for clarity, and they just show details, which are essential to the understanding of the invention, while other details are left out. Throughout, the same reference numerals are used for identical or corresponding parts.

As shown in FIGS. 7–8, the incremental indentations 135 of the dose setting button 105 is preferably located on a circular curved track 138 provided adjacent the upper part 139 of the dose setting button 105. The upper part 139 is also provided with a finger grip 140, by which the user can grip when setting up the dose to be injected.

The carrier 143 provided on the backside of the dose setting button 105 connects the dose setting button with the coupling ring 118 such that the coupling ring 118 rotates with the dose setting button 105.

The distance between the indentations 135 determines the size of the dose volume to be set. With the distance between the indentations 135 shown in FIG. 7 some rather large dose volumes are set. Preferably the number of the indentations 135 should be a multiplication of the number of teeth provided on the outer toothing 117 of the driver 116. If the injection device e.g. is made with 60 teeth on the outer toothing 117, there should be 2, 3, 5, 6, 10, 12, 15, 20, 25, 30, or 60 indentations 135 such that the overriding dose setting clicks works with the underlying dose setting mechanism on the full circle.

It is however possible to have a number of indentations which are not a multiplication of the numbers of teeth on the driver 116 as long as one dose setting on the dose setting button 105 correlates with a full number of teeth on the outer toothing 117 of the driver 116. In such case however the full circle can not be utilized.

When a large distance between the indentations 135 corresponding to large dose volumes, is used, it is beneficial to provide a separate air shoot click 141 provided between the first and the second of the indentations 135. In this way, the user can use this small air shoot click 141 when making an air shoot instead of having to use a full dose volume.

The distance between the indentations 142 of the dose setting button 105, is in FIG. 8 shown as a short distance corresponding to a small dose volume. The specific dose setting button 105 shown in FIG. 8 has 60 indentations 142 on one full circle, such that the scale can be made to resemble that of an ordinary egg timer such as shown in U.S. Pat. No. 5,947,934.

Some preferred embodiments have been shown in the foregoing, but it should be stressed that the invention is not limited to these, but may be embodied in other ways within the subject matter defined in the following claims.

| Listing of parts | | |
|---|---|---|
| 1 | Injection device | |
| 2 | Dose setting and injecting mechanism | 102 |
| 3 | Housing | |
| 4 | Cartridge | |
| 5 | Dose setting button | 105 |

-continued

Listing of parts

| | | |
|---|---|---|
| 6 | Injection button | 106 |
| 7 | Toothed rack | 107 |
| 8 | Rod guiding part | 108 |
| 9 | Piston rod | 109 |
| 10 | Slot | |
| 11 | First gear wheel | 111 |
| 12 | Hub-wheel | |
| 13 | Second gear wheel | 113 |
| 14 | Outer toothed wheel | |
| 15 | Toothed axis | 115 |
| 16 | Driver | 116 |
| 17 | Outer toothing of Driver | 117 |
| 18 | Coupling ring | 118 |
| 19 | Coupling ring wheel | 119 |
| 20 | Rigid part | |
| 21 | Flexible part | |
| 22 | Barbs | 122 |
| 23 | Protrusion | 123 |
| 24 | Arm | |
| 25 | Centre of arm | |
| 26 | Cam | |
| 27 | Notch | |
| 28 | Depression | |
| 29 | Second arm | |
| 30, 31 | Bulging ends (of coupling ring) | 131, 132 |
| 32 | inside surface | 132 |
| | | 133 |
| | | 134 |
| | Indentations | 135, 142 |
| | Protrusion | 136 |
| | Flexible arm | 137 |
| | Curved track | 138 |
| | Upper part (of Dose setting button) | 139 |
| | Finger grip | 140 |
| | Carrier | 143 |

What is claimed is:

1. An injection device having a housing accommodating a cartridge containing medicine sufficient for a number of dosed injections, which doses are injected by advancing a piston rod forward inside the cartridge, comprising:
    a dose setting and injection mechanism, comprising an incremental feedback mechanism,
    a rotatable dose setting member operationally coupled to the dose setting and injection mechanism for setting up a dose to be injected, and
    an injection button operationally coupled to the dose setting and injection mechanism and by which the dose setting and injection mechanism can be activated for advancing the piston rod forward to press out the set dose through a conduit connected to said cartridge,
    wherein:
    an additional clicking means is provided between the rotatable dose setting member and a non-rotatable clicker element, and wherein the additional clicking means provides incremental clicks corresponding to a dose volume,
    the clicking means comprises a curved track provided as a part of the rotatable dose setting member wherein curved track engages the non-rotatable clicker element provided on or as a part of the injection device,
    the curved track is provided with a number of spared indentations,
    there are 5 to 60 equally spaced indentations, and
    an air shot indentation is provided between the first equally spaced indentations.

2. An injection device having a housing accommodating a cartridge containing medicine sufficient for a number of dosed injections, which doses are injected by advancing a piston rod forward inside the cartridge, comprising:
    a dose setting and injection mechanism, comprising an incremental feedback mechanism,
    a rotatable dose setting member operationally coupled to the dose setting and injection mechanism for setting up a dose to be injected, and
    an injection button operationally coupled to the dose setting and injection mechanism and by which the dose setting and injection mechanism can be activated for advancing the piston rod forward to press out the set dose through a conduit connected to said cartridge,
    wherein:
    an additional clicking element is provided between the rotatable dose setting member and a non-rotatable clicker element, and wherein the additional clicking element provides incremental clicks corresponding to a dose volume,
    the clicking element comprises a curved track provided as a part of the rotatable dose setting member wherein curved track engages the non-rotatable clicker element provided on or as a part of the injection device,
    the curved track is provided with a number of equally spaced indentations, there are more than 2 spaced indentations, and
    an air shot indentation is provided between the two first equally spaced indentations.

* * * * *